United States Patent [19]

Houlgrave et al.

[11] Patent Number: 4,770,248

[45] Date of Patent: Sep. 13, 1988

[54] DEVICE TO ORIENT ELECTRICAL CONNECTORS IN A SUBSEA WELL

[75] Inventors: Robert C. Houlgrave, Houston; Thomas J. Ames, Cypress; Anthony J. Masciopinto, Kingwood; Glen H. Cuiper, Spring, all of Tex.; Gary A. Shaw, Milltown, Scotland

[73] Assignee: Hughes Tool Company, Houston, Tex.

[21] Appl. No.: 1,314

[22] Filed: Jan. 8, 1987

[51] Int. Cl.⁴ .......................................... E21B 33/043
[52] U.S. Cl. ..................................... 166/341; 166/65.1
[58] Field of Search .............. 166/341, 349, 385, 65.1; 29/689

[56] References Cited

U.S. PATENT DOCUMENTS

| | | |
|---|---|---|
| 1,851,319 | 3/1932 | McCoy et al. |
| 2,416,441 | 2/1947 | Grant et al. |
| 2,750,569 | 6/1956 | Moon |
| 3,070,166 | 12/1962 | Knauth |
| 4,154,302 | 5/1979 | Cugini ........................... 166/65.1 X |
| 4,363,168 | 12/1982 | Bryer et al. ..................... 166/341 X |
| 4,416,495 | 11/1983 | Regan |
| 4,627,489 | 12/1986 | Reed ................................. 166/65.1 |

OTHER PUBLICATIONS

Petroleum Productions Engineering (uren 1956, pp. 552 & 553).

Primary Examiner—Stephen J. Novosad
Attorney, Agent, or Firm—James E. Bradley

[57] ABSTRACT

A method and apparatus for making an electrical connection through a tubing hanger in a subsea well avoids the need for precise gauging and alignment. The tubing hanger has an electrical receptacle located on its rim and a guide hole also located on the rim. An impression block tool is lowered into the wellhead from the surface to make an impression of the rim to determine the orientation of the guide hole. A carrier is mounted to the tree connector at the surface. The carrier has a guide pin and an electrical connector. The carrier is aligned, then secured to the tree connector so that it can move only a limited amount rotationally. As the tree connector enters the wellhead, the guide pin will enter the guide hole, which is tapered. A limited amount of rotation of the carrier relative to the tree connector allows the electrical connectors to precisely align before contacting each other.

5 Claims, 5 Drawing Sheets

DEVICE TO ORIENT ELECTRICAL CONNECTORS IN A SUBSEA WELL

BACKGROUND OF THE INVENTION

1. Field of the Invention:

This invention relates in general to subsea well installations, and in particular to a device and method for making electrical connections through a tubing hanger.

2. Description of the Prior Art:

In a producing oil or gas well, useful information can be obtained by monitoring the pressure and the temperature at the bottom of the well. One method of monitoring the pressure and temperature is by using a pressure and temperature sensor located near the producing formation, and connected by an electrical wire that extends upward to the surface for readout on surface instruments. A tubing hanger located at the top of the well supports the production tubing and seals the upper end of the tubing in the casing. An electrical connection will be made at the tubing hanger for the pressure and temperature wires.

Making this electrical connection presents a problem in a subsea well. In a subsea well of the type that has the Christmas tree mounted at the wellhead on the subsea floor, the tubing hanger will be located possibly hundreds of feet from the surface of the water. When completing the well for production, a floating vessel will lower a Christmas tree connector onto the wellhead located on the sea floor. The Christmas tree connector has a stinger that inserts into the bore of the tubing hanger. It also has an electrical connector for mating with an electrical connector located in the tubing hanger if pressure and temperature monitoring is to be used. Aligning the electrical connectors with each other is time consuming, because the precise orientation of the electrical connector located in the tubing hanger is not known. One type of electrical connection in a tubing hanger uses concentric rings. While no orientation is needed, the ring connector is expensive to manufacture.

SUMMARY OF THE INVENTION

In this invention, the tubing hanger has one or more electrical connections located in receptacles on its rim, all offset from the axis of the tubing hanger. There is also a guide hole, which is elongated on its upper end and tapers down to a cylindrical portion. A carrier is mounted to the tree connector.

The carrier has an orienting or guide pin that is adpated to be inserted into the bevelled guide hole as the tree connector is lowered down over the wellhead. The carrier also supports the electrical connectors for connecting with the electrical connectors in the tubing hanger. The carrier is allowed a limited amount of rotational movement with respect to the Christmas tree connector.

To assure that the guide pin is located so as to contact part of the guide hole, an impression block tool is first lowered into the well to determine the location of the guide hole relative to a known reference point on the wellhead. This impression block tool has an impression plate that when pushed downwardly, makes an impression of the rim of the tubing hanger. This locates the guide hole to the reference point.

DESCRIPTION OF THE PREFERRED EMBODIMENT

Figure 1:
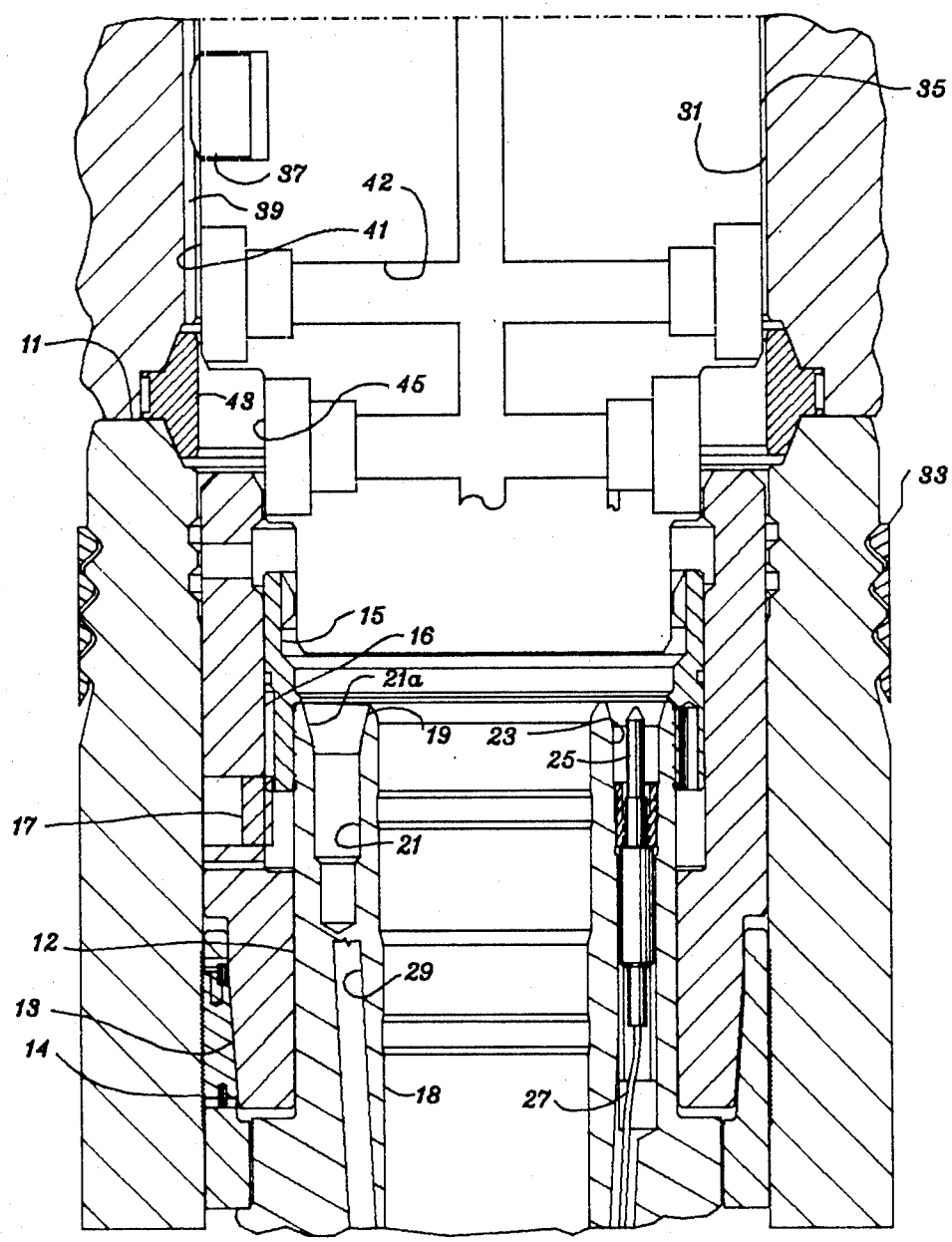
FIG. 1 is a vertical sectional view of a wellhead having a tubing hanger contained therein, and showing an impression block tool in the process of being lowered into the wellhead.

Referring to FIG. 1, subsea wellhead 11 has a tubing hanger 12 mounted in its interior. The tubing hanger 12 is supported conventionally by a wedge ring 13. The wedge ring 13 wedges slips 14 outward into engagement with small parallel grooves or wickers formed in the interior of the wellhead 11. The tubing hanger 12 is connected to a string of tubing (not shown) extending down into the well.

The tubing hanger 12 and the tubing have been lowered into place with a running tool (not shown), which grips a reaction sleeve 15 rigidly secured to the upper edge of the tubing hanger 12. The running tool grips the reaction sleeve 15 and hydraulically pushes down on the wedge ring 13 to force the slips 14 outward into engagement. The wedge ring 13 is guided by a slot 16 formed in the reaction sleeve 15 and a key 17 inserted into the wedge ring 13.

Figure 2:
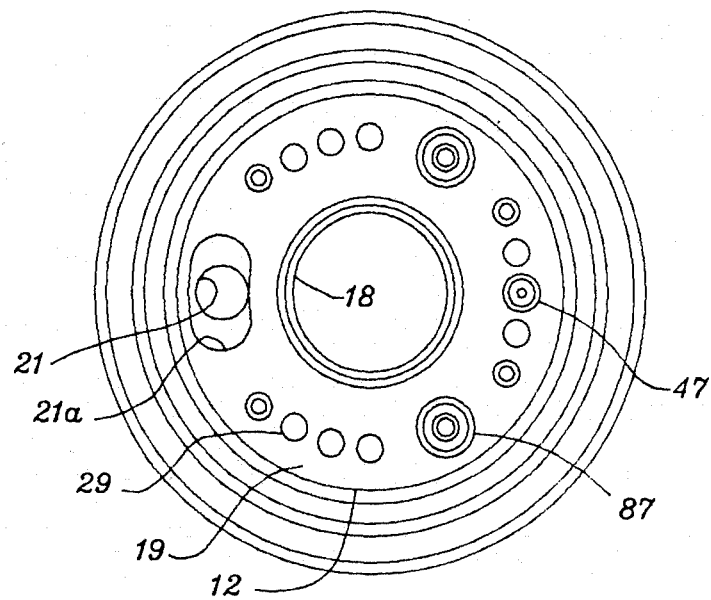
FIG. 2 is a top view of a tubing hanger constructed in accordance with this invention.
Figure 3:
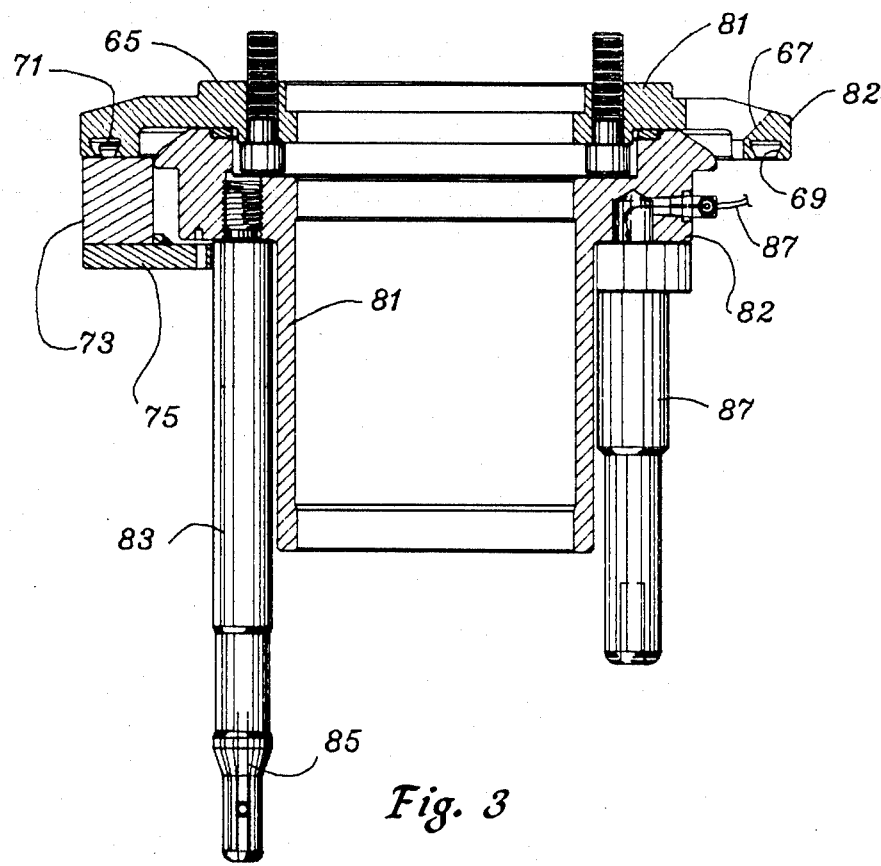
FIG. 3 is a vertical sectional view of a carrier for carrying the guide pin and the upper electrical connectors for mating with the electrical connectors of the tubing hanger of FIG. 1.

Tubing hanger 12 has a bore 18 and an upper rim 19. A guide hole 21 is drilled downwardly from the rim 19 into the wall of the tubing hanger 12. As shown in FIG. 2, guide hole 21 is elongated on its upper end 21a. The elongated upper end 21a is bevelled and tapers downwardly to a cylindrical portion shown in FIG. 1. The cross-sectional area of the upper end 21a is substantially greater than the cross-sectional area of the lower cylindrical portion.

There are also two electrical receptacles or holes 23, each for containing an electrical contact 25. The electrical receptacles 23 are spaced apart from each other as shown in FIG. 2. Each electrical contact 25 in the preferred embodiment is a male pin, and is connected to a downhole wire 27 which extends downwardly to a pressure or temperature gauge (not shown). There is also one or more annulus passages 29 which extend through the tubing hanger 12 for communicating fluid from the annulus between the tubing and casing (not shown) with passages located above.

In FIG. 1, the blowout preventer connector 31 used prior to landing a Christmas tree is connected to the wellhead 11 by dogs 33. The blowout preventer connector 31 connects to a riser (not shown) which is a string of large diameter conduit that extends to the floating vessel (not shown). Four guide posts (not shown) are positioned around the blowout preventer connector 31. Each guide post is connected to a cable that extends to the floating vessel.

An impression block tool 35 is shown being lowered through the riser into the wellhead 11. The impression block tool 35 is lowered on a string of drill pipe (not shown) from the floating vessel. The impression block tool 35, once lowered into place, is rotated until a dog or key 37 on its side wall springs outwardly and snaps into a slot 39 located in the blowout preventer connector 31.

The orientation of the slot 39 in the blowout preventer connector 31 relative to the position of the floating vessel will be known at the surface. Notice of the orientation of the slot 39 was previously made at the surface when the blowout preventer connector 31 was lowered into place using the four guide cables. The guide cables and guide posts assure that the slot 39 will be aligned in a known direction once the blowout preventer connector 31 lands and thus is a known reference point.

The impression block tool 35 has an impression plate assembly 41 on its side wall, which includes an impression plate or soft metal, such as lead or babbitt mounted to a piston (not shown) and connected with hydraulic passages 42. Supplying hydraulic fluid to the hydraulic passages 42 pushes the impression plate assembly 41 outwardly to make an impression on the plate assembly 41 as a result of contact with an annular seal 43 which is located on the upper rim of the wellhead 11.

There is also an impression plate assembly 45 connected to the hydraulic passages 42 and located on the side wall of the impression block tool 35 below the impression plate assembly 41. When pushed outwardly, the impression plate assembly 45 makes an impression as a result of contact with the upper interior of the reaction sleeve 15. The lower end of the impression block tool 35 contacts the rim 19 of the tubing hanger 12 to make an impression.

Figure 7:
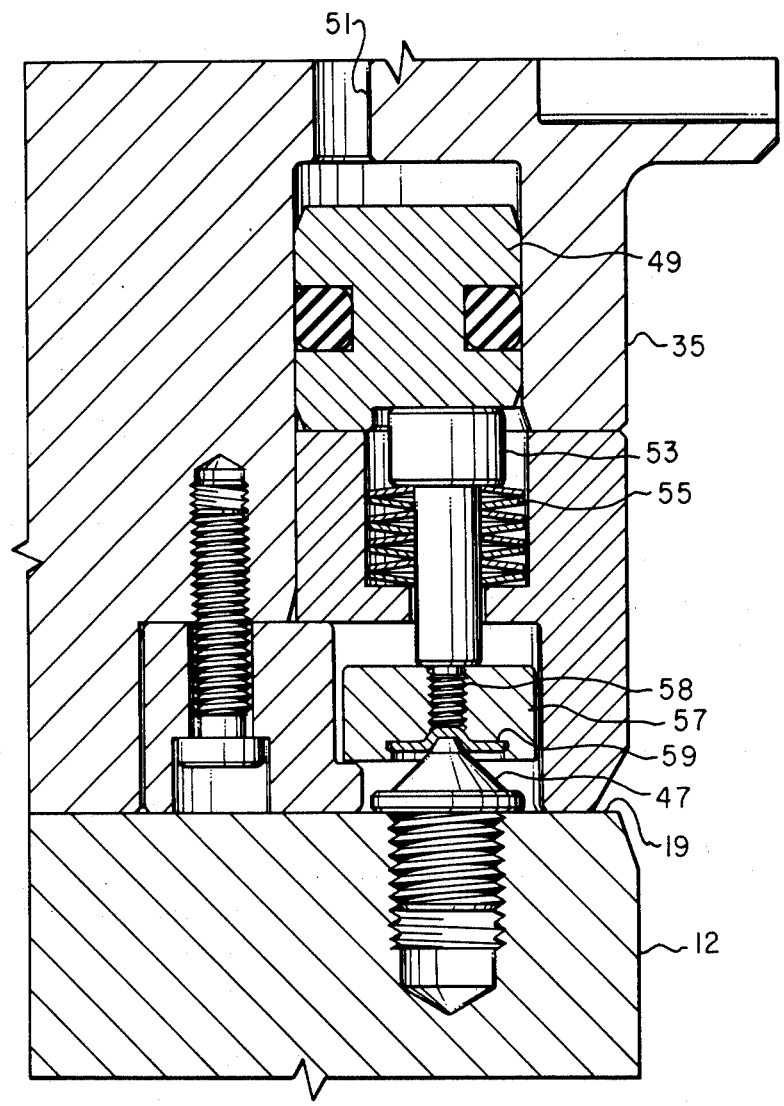
FIG. 7 is an enlarged partial sectional view of a portion of the impression block tool shown in FIG. 1.

A portion of the lower end of impression block tool 35 is shown in sectional view in FIG. 7. The tubing hanger 12 has a marking projection 47 comprising a conical protuberance mounted to the rim 19. An annular piston 49 is reciprocally carried in the body of the impression block tool 35. Piston 49 communicates with a hydraulic fluid passage 51, which leads to the hydraulic fluid passages 42 as shown in FIG. 1. Piston 49 bears against a plurality of push rods 53. Each push rod 53 is encircled by a number of Belleville washers 55, which bias the push rods 53 upward when the piston 49 pushes downwardly against them.

The push rods 53 contact a holder 57 to push it downward. Holder 57 has an impression plate 59 of lead or babbit located in a recess on its lower end. Impression plate 59 is annular and will deform as shown in FIG. 7 when pressed against the marking projection 47. Holes 58 formed in the holder 57 accommodate the deformation of the impression plate 59. The impression block tool 35, when retrieved to the surface, will thus provide the orientation of the guide hole 21 (FIG. 1) which is located 180 degrees from the marking projection 47. The orientation will be relative to the slot 39, whose true direction is known at the surface.

Figure 6:
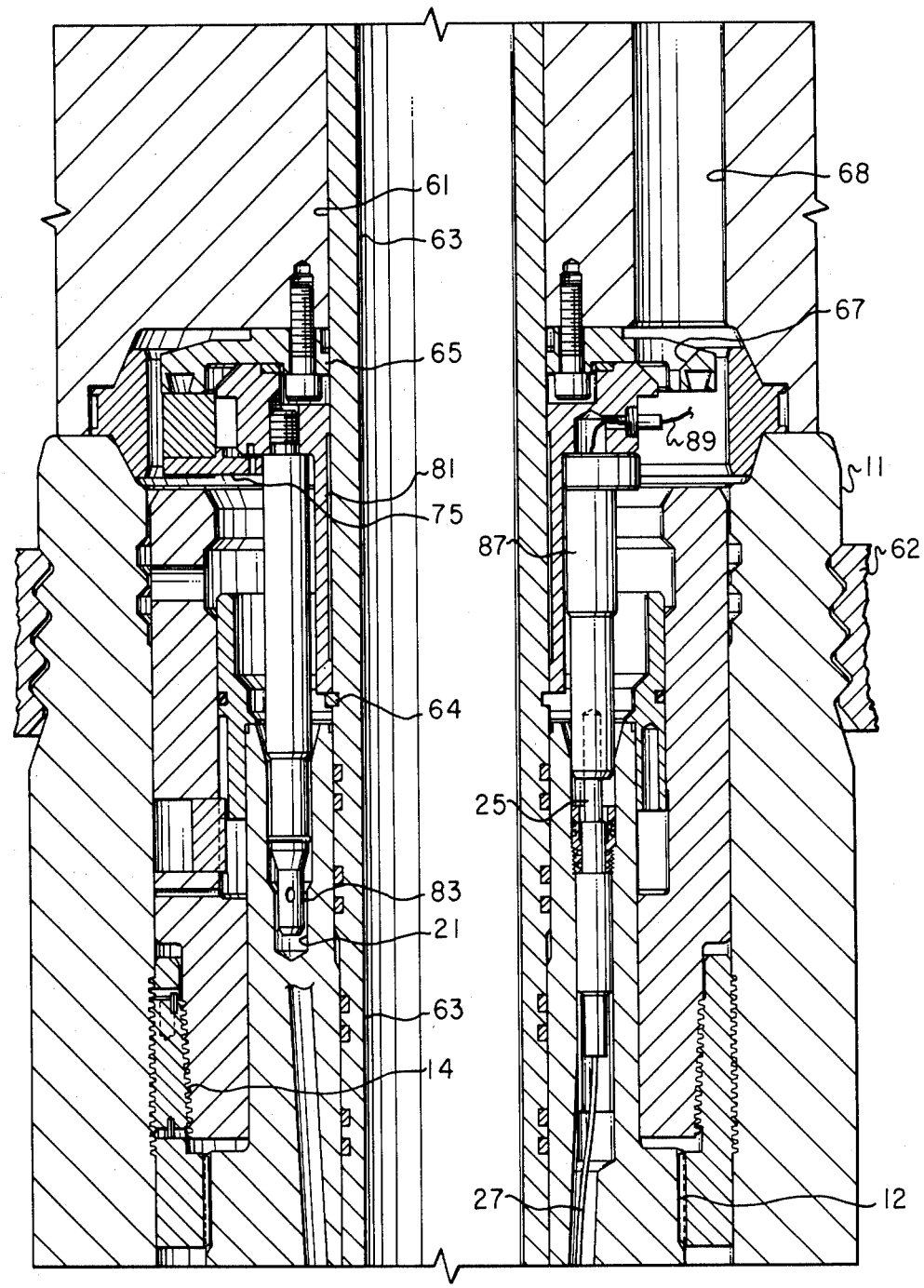
FIG. 6 is a vertical sectional view of a subsea wellhead, with the Christmas tree and the electrical connections in place.

Referring to FIG. 6, after the impression block tool 35 is retrieved, the blowout preventer connector 31 (FIG. 1) is retrieved along with the drilling riser (not shown). Then, a Christmas tree connector 61 is lowered into place, as shown in FIG. 6. Christmas tree connector 61 comprises the lower end of a Christmas tree and secures to the wellhead 11 with dogs 62. The Christmas tree connector 61 also is lowered on the guide cables over guide posts (not shown), thus its true directional orientation will be known at the surface. The Christmas tree connector 61 has a tubular stinger or mandrel 63 which extends downwardly into the bore 18 of the tubing hanger 12. Produced fluids will flow through the stinger 63 to a production riser (not shown) to the surface.

Stinger 63 has a retaining ring 64 located on its exterior and positioned to locate just above the rim 19 of the tubing hanger 12. Stinger 63 is bolted to the Christmas tree connector 61 by means of a support ring 65. Support ring 65 has an annular passage 67 to allow fluid to flow from the tubing annulus through the annulus passages 29 to a passage 68 in the Christmas tree connector 61.

The support ring 65 has a groove 69 that is annular and faces downwardly. Groove 69 is "dove-tailed" in configuration. As shown also in FIG. 4, a pair of threaded bolts or pins 71 are slidingly received in the annular groove 69. Each pin 71 is secured by threads to a spacer 73 and has a dove-tailed head that is slidingly carried in the groove 69. A bracket 75 is mounted to the lower end of the spacer 73 by bolts 77, shown in FIG. 4. Bracket 75 has a pair of spaced apart arms 79 that extend inwardly and are shown in FIG. 4.

Figure 5:
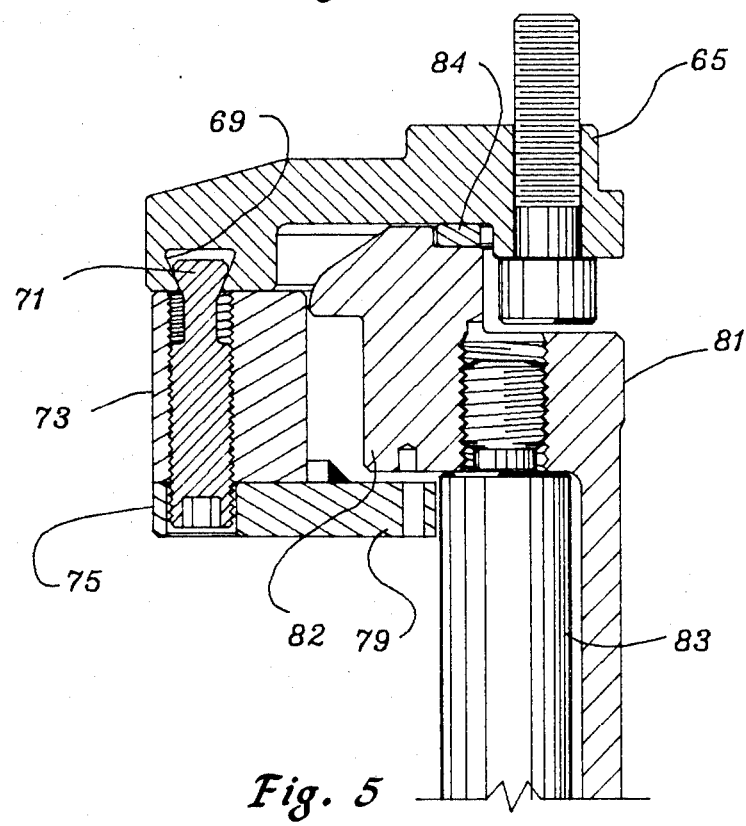
FIG. 5 is a partial enlarged sectional view of the carrier of FIG. 3.

A carrier sleeve 81, shown in FIGS. 5 and 6, is rotatably carried by the stinger 63 and supported on the retaining ring 64. The carrier sleeve 81 has an annular rim 82. A bearing 84 located between rim 82 and support ring 65 facilitates rotation of the carrier sleeve 81. A guide pin 83 is mounted to the rim 82 and extends downwardly for engaging the guide hole 21. The guide pin 83 has a passage 85 on its lower end for displacing fluid as the guide pin 83 enters the guide hole 21. The lower portion of guide pin 83 is of smaller diameter than the upper portion.

There are also two electrical connectors 87 mounted to the rim 82 of the carrier sleeve 81. The electrical connectors 87 have female connectors on the lower ends to slide over the electrical connectors 25. The electrical connectors 87 connect to uphole wires 89 (FIG. 6) which lead into the tree connector 61 and to the surface. The guide pin 83 is longer than the electrical connectors 87.

Figure 4:
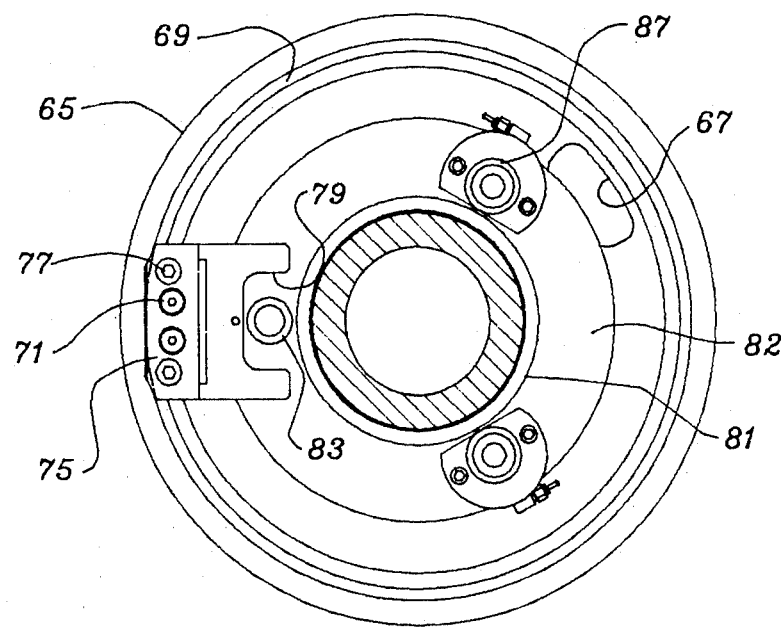
FIG. 4 is a bottom view of the carrier of FIG. 3.

Referring to FIG. 4, the guide pin 83 is located between the arms 79 of the bracket 75. The distance between the arms 79 is about twice that of the diameter of the guide pin 83. The carrier sleeve 81 is free to pivot or rotate relative to the stinger 63 (FIG. 6), until the guide pin 83 contacts one of the arms 79. The amount of rotation allowed is in the range fron 10 to 20 degrees in either direction from the center point between the arms 79.

In operation, referring first to FIG. 1, the tubing hanger 12 will be lowered into place in the wellhead 11 through the interior of the blowout preventer connector 31. The running tool (not shown) for the tubing hanger 12, will grip the reaction sleeve 15 and push downwardly on the wedge ring 13, wedging the slips 14 outwardly to grip the wellhead 11. The running tool will be removed to the surface.

At this point, it will not be known precisely how far the rim 19 of the tubing hanger 12 is from the seal 43, nor will it be known where the guide hole 21 is located. To determine these unknowns, the impression block tool 35 is lowered through the blowout preventer connector 31 until its lower end contacts the rim 19. The impression block tool 35 is rotated until its spring loaded dog 37 engages the slot 39 contained in the blowout preventer connector 31. Then, hydraulic fluid pressure is supplied to the passages 42 to push out the impression plates 41 and 45 as shown in FIG. 1. The hydraulic fluid pressure in the passages 42 also pushes the impression plate 59 downwardly into contact with the marking projection 47 located on top of the tubing hanger 12, shown in FIG. 7. The impression block tool 35 is then retrieved.

The orientation of the slot 39 is known, and from this, the orientation of the marking projection 47 relative to the slot 39 can be determined by looking at the impression in the impression plate 59. Also, the distance from the rim 19 of the tubing hanger 12 to the seal 43 can be determined by measuring the distance from the mark formed on the impression plate 41 to the bottom of the impression block tool 35. In addition, by measuring the impression on the impression plate 45 relative to the bottom of the impression block tool 35, one can determine at the surface whether or not the wedge ring 13 was fully stroked down to properly set the tubing hanger 12.

Prior to lowering the Christmas tree connector 61, the lengths of the guide pin 83 and electrical connectors 87 (FIG. 6) can be increased, if necessary, by inserting spacers (not shown) to assure that the length is commensurate with the distance from the rim 19 to the seal 43. Then, while still at the surface, the carrier sleeve 81 is rotated to position it for alignment with the guide hole 21. For example, the blowout preventer connector 31 may have been run with the slot 39 located halfway between guide cables identified as the number one and number two cables. If the marking projection 47 indicated that it was located 180 degrees from slot 39, then the guide pin 83 would be positioned on the tree connector 61 halfway between cables number one and number two, because the guide hole 21 is located 180 degrees from marking projection 47.

To rotate the bracket 75 and the carrier sleeve 81 relative to the support ring 65, it will be necessary to loosen the pins 71. Loosening the pins 71 reduces the frictional contact between the spacer 73 and the support ring 65, as shown in FIG. 5. This allows one to freely slide the bracket 75 and the carrier sleeve 81 around the support ring 65, with the pins 71 sliding in the groove 69. Once the guide pin 83 is oriented at the proper point, the pins 71 are tightened. This rigidly locks the bracket 75 to the support ring 65.

The carrier sleeve 81 then can rotate only until the guide pin 83 strikes one or the other of the arms 79, as shown in FIG. 4. The bracket 75, the carrier sleeve 81, and associated components serve as orienting means for aligning the guide pin 83, and for limiting the degree of rotation of the guide pin around the stinger 63 once in the aligned position.

The blowout preventer connector 31 is removed, along with the drilling riser. The carrier sleeve 81 is assembled to the Christmas tree connector 61, and the Christmas tree connector 61 is lowered in place, using the guide cables and guide posts (not shown). In this manner, rotational orientation of the guide pin 83 will remain the same as the Christmas tree connector 61 is lowered into the sea and placed onto the wellhead 11.

After the stinger 63 enters the bore 18 of the tubing hanger 12, shown in FIG. 6, the guide pin 83 will enter the guide hole 21. The guide pin 83 is longer than the electrical connectors 87, and will enter the guide hole 21 before the electrical connectors enter the receptacles 23. The elongated tapered guide hole 21, as shown in FIG. 2, and the reduced diameter lower end of guide pin 83, allow the guide pin 83 to be located out of alignment several degrees in each direction from the cylindrical lower portion of the guide hole 21. If not precisely aligned, the guide pin 83, as it contacts the guide hole 21, will rotate the carrier sleeve 81 relative to the stinger 63 due to the taper of the guide hole 21. As the guide pin 83 enters the cylindrical portion of the guide hole 21, it will have rotated the carrier sleeve 81 to precisely align the electrical connectors 87 before they contact the electrical receptacles 23.

When the connectors 87 join the contacts 25, as shown in FIG. 6, electrical continuity will exist between the downhole wire 27 and the uphole wire 89. This establishes electrical continuity between pressure and temperature sensors (not shown) at the bottom of the well and indicating instruments at the surface.

The invention has significant advantages. Using the impression block tool to mark on a projection on the tubing hanger, enables one at the surface to properly align the electrical connectors prior to running the tree conductor into the sea. The dove-tailed groove and bracket arms prevent the electrical connectors from rotating far out of orientation as the tree connector is lowered into the sea. The spaced apart arms of the bracket surrounding the guide pin, allow a limited amount of rotation. This limited amount of rotation, coupled with the elongated tapered guide hole, causes the electrical connectors to precisely align with each other, even though they may have been missaligned by several degrees at the surface.

While the invention has been shown in only one of its forms, it should be apparent to those skilled in the art that it is not so limited, but is susceptible to various changes without departing from the scope of the invention.

We claim:

1. In a subsea well having a tree connector mounted to a wellhead, the wellhead containing a tubing hanger having an axial bore for receiving a tubular stinger extending from the tree connector, a downhole electrical wire extending downwardly from the tubing hanger, and an uphole electrical wire extending upwardly from the tree connector, the improvement comprising in combination:

at least one upwardly facing electrical socket located on the rim of the tubing hanger and having an axis offset from the axis of the tubing hanger, the socket being connected to the downhole wire;

an upwardly facing guide hole located on the rim of the tubing hanger and tapering downwardly, the guide hole being spaced away from the socket and having an axis parallel to the axis of the socket;

a carrier mounted to the tree connector adjacent to the stinger;

a guide pin and an electrical connector mounted to the carrier and spaced apart from each other for reception in the guide hole and the socket, respectively, the electrical connector being connected to the uphole wire; and orienting means for positioning at the surface the guide pin and carrier relative to the tree connector to a substantially aligned position with the guide hole, and for allowing the carrier to rotate relative to the tree connector about the axis of the tree connector, but only to a selected amount, once the carrier is in the aligned position, to enable the guide pin to rotate the electrical connector into precise alignment with the socket as the guide pin slides into the tapered guide hole.

2. In a subsea well having a tree connector mounted to a wellhead, the wellhead containing a tubing hanger having an axial bore for receiving a tubular stinger extending from the tree connector, a downhole electrical wire extending downwardly from the tubing hanger, and an uphole electrical wire extending upwardly from the tree connector, the improvement comprising in combination:

at least one upwardly facing electrical socket located on the rim of the tubing hanger and having an axis offset from the axis of the tubing hanger, the socket being connected to the downhole wire;

an upwardly facing tapered guide hole located on the rim of the tubing hanger;

an impression block tool adapted to be lowered onto the tubing hanger and retrieved prior to lowering the tree connector onto the wellhead;

an annular impression plate located on the lower end of the impression block tool;

means including a slot in the tree connector for providing a known reference point;

key means on the impression block tool for engaging the slot provided in the subsea well for orienting the impression block tool relative to the known reference point;

means for pushing the impression plate into contact with the rim of the tubing hanger to form an impression in the impression plate to determine the position of the guide hole relative to the known reference point;

a carrier mounted to the tree connector adjacent the stinger;

a guide pin and an electrical connector mounted to the carrier for reception in the guide hole and the socket, respectively, the electrical connector being connected to the uphole wire;

orienting means for positioning the carrier relative to the tree connector to an aligned position relative to the known reference point, based on the impression taken on the impression plate prior to lowering the tree connector onto the wellhead, and for allowing the carrier to rotate relative to the tree connector, but only to a selected degree, once the carrier is in the aligned position, to enable the guide pin to rotate the carrier to precisely align the electrical connector as the guide pin enters the tapered guide hole.

3. In a subsea well having a tree connector mounted to a wellhead, the wellhead containing a tubing hanger having an axial bore for receiving a tubular stinger extending from the tree connector, a downhole electrical wire extending downwardly from the tubing hanger, and an uphole electrical wire extending upwardly from the tree connector, the improvement comprising in combination:

at least one upwardly facing electrical socket located on the rim of the tubing hanger and having an axis offset from the axis of the tubing hanger, the socket being connected to the downhole wire;

an upwardly facing guide hole located on the rim of the tubing hanger, the guide hole tapering downwardly from a larger cross-sectional area on its upper end to a smaller cross-sectional area on its lower end, the guide hole being spaced away from the socket and having an axis parallel to the axis of the socket;

means in the tree connector for providing a known reference point;

means for determining the position of the guide hole relative to the known reference point after the tubing hanger is installed in the wellhead;

an annular carrier mounted to the tree connector and encircling the stinger;

a guide pin and electrical connector spaced apart from each other and protruding downwardly from the carrier for reception in the guide hole and socket, respectively, the pin being of greater length than the electrical connector; and orienting means for allowing free rotation of the carrier relative to the tree connector at the surface to a substantially aligned position with the guide hole and the socket, and for limiting to a selected amount rotational movement of the carrier relative to the tree connector about the axis of the tree connector when in the substantially aligned position, allowing some rotational movement as the guide pin enters the tapered guide hole to precisely align the electrical connector.

4. In a subsea well having a tree connector mounted to a wellhed, the wellhead containing a tubing hanger having an axial bore for receiving a tubular stinger extending from the tree connector, a downhole electrical wire extending downwardly from the tubing hanger, and an uphole electrical wire extending upwardly from the tree connector, the improvement comprising in combination:

at least one upwardly facing electrical socket located on the rim of the tubing hanger and having an axis offset from the axis of the tubing hanger, the socket being connected to the downhole wire;

an upwardly facing guide hole located on the rim of the tubing hanger, the guide hole tapering downwardly from a larger cross-sectional area on its upper end to a smaller cross-sectional area on its lower end;

an annular carrier rotatably mounted to the tree connector and encircling the stinger;

a guide pin and electrical connector spaced apart from each other and protruding downwardly from the carrier, the pin being of greater length than the electrical connector;

a bracket mounted to the tree connector adjacent the stinger, the bracket having a pair of spaced apart arms extending below the carrier and receiving between them the guide pin, the distance between the arms being greater than the diameter of the guide pin; and means for rigidly mounting the bracket to the tree connector in an aligned position to orient the guide pin substantially in alignment with the guide hole, the distance between the arms allowing a selected amount of rotation of the carrier relative to the tree connector to accommodate misalignment as the guide pin enters the tapered guide hole.

5. A method of electrically coupling an uphole wire leading upwardly from a tree connector to a downhole wire leading downwardly from a tubing hanger located in a subsea wellhead, comprising:

providing at least one electrical socket on the rim of the tubing hanger, with an axis offset from the axis of the tubing hanger and connected into the downhole wire;

providing a guide hole in the rim of the tubing hanger;

locating the tubing hanger in the wellhead;
providing a known reference point in the tree connector;
lowering an impression block tool in the wellhead and pushing an impression block plate on the lower end of the impression block tool into contact with the rim of the tubing hanger to make a permanent impression and determine the position of the guide hole relative to the known reference point;
rotatably mounting a carrier sleeve to the tree connector, the carrier sleeve having a guide pin and an electrical connector, and orienting the guide pin prior to lowering it into the wellhead to a substantially aligned position based on the impression plate measurement;
securing the carrier so that it can rotate relative to the tree connector only a limited amount once it is in the aligned position; and
lowering the tree connector onto the wellhead with the guide pin entering the guide hole and the electrical connector entering the electrical socket, if needed the guide pin rotating the carrier up to said limited amount to align the electrical connector as the guide pin enters the guide hole.

* * * * *